(12) United States Patent
Horiguchi et al.

(10) Patent No.: US 7,410,350 B2
(45) Date of Patent: Aug. 12, 2008

(54) AMPUTATED PART HOLDING APPARATUS AND METHOD FOR MAKING MOULD OF AMPUTATED PART

(75) Inventors: Tomohiko Horiguchi, Osaka (JP); Yoichi Takada, Osaka (JP)

(73) Assignee: Kawamura Gishi Co., Ltd. (JP)

( * ) Notice: Subject to any disclaimer, the term of this patent is extended or adjusted under 35 U.S.C. 154(b) by 681 days.

(21) Appl. No.: 10/686,366

(22) Filed: Oct. 14, 2003

(65) Prior Publication Data

US 2004/0076700 A1 Apr. 22, 2004

(30) Foreign Application Priority Data

Oct. 18, 2002 (JP) .............................. 2002-304836

(51) Int. Cl.
*B28B 1/00* (2006.01)
(52) U.S. Cl. ..................... 425/2; 425/389; 425/405.1
(58) Field of Classification Search ............... 425/2, 425/389, 405.1; 264/222, 223, DIG. 30
See application file for complete search history.

(56) References Cited

U.S. PATENT DOCUMENTS

| | | | | |
|---|---|---|---|---|
| 2,472,754 A | * | 6/1949 | Mead | 264/DIG. 30 |
| 2,488,922 A | * | 11/1949 | Mead | 264/DIG. 30 |
| 2,517,902 A | * | 8/1950 | Luebkeman | 264/DIG. 30 |
| 3,962,395 A | * | 6/1976 | Hagglund | 264/222 |
| 4,906,425 A | * | 3/1990 | Poussou | 425/2 |
| 6,709,617 B2 | * | 3/2004 | Wu | 425/2 |

FOREIGN PATENT DOCUMENTS

| | | | | |
|---|---|---|---|---|
| GB | 2116432 A | * | 9/1983 | |
| GB | 2149309 A | * | 6/1985 | |
| JP | 2003-265507 | | 9/2003 | |

OTHER PUBLICATIONS

JSPO Journal, vol. 14 (2), p. 176-178, published on Apr. 1, 1998.
JSPO Journal, vol. 16 (supplement), p. 114-115, published on Sep. 1, 2000.
PO Academy Journal, vol. 9 (2), p. 109-110, published on Sep. 2001.
Substitutability of Negative Pressure Particle Bag in Materials for Prosthetic and Orthoses by Kazuhiko Sasaki et al., published Oct. 15, 2001 in "Proceedings of the 17th Scientific Meeting of the Japanese Society of Prosthetics and Orthotics".

* cited by examiner

*Primary Examiner*—Robert B Davis
(74) *Attorney, Agent, or Firm*—Gerald E Hespos; Anthony J Casella

(57) ABSTRACT

An amputated part holding apparatus has a contact member provided in a casing to define a particle charge chamber between the contact member and the casing. The contact member comes into pressing contact with an amputated part owing to increased pressure in the particle charge chamber. The chamber is charged with particles to generate pressing force. The amputated part holding apparatus is further provided with a particle supply unit including a particle charging device.

6 Claims, 17 Drawing Sheets

FIG.12
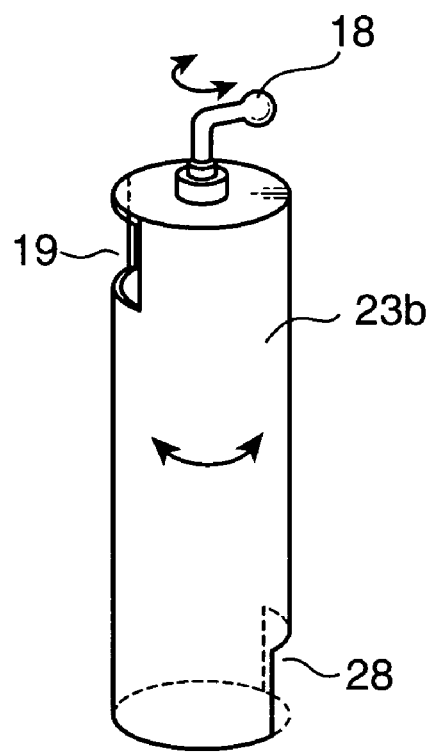
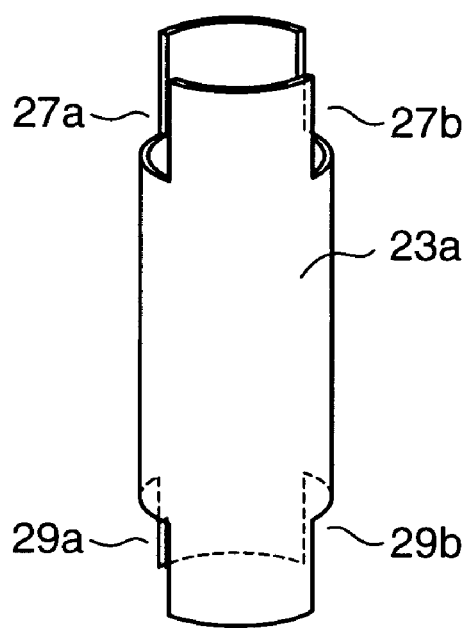

AMPUTATED PART HOLDING APPARATUS AND METHOD FOR MAKING MOULD OF AMPUTATED PART

BACKGROUND OF THE INVENTION

1. Field of the Invention

This invention relates to an amputated part holding apparatus which is used to make a mould of an amputated part of a human body for production of a prosthesis, and to enable virtual experience of putting on a prosthesis, and a method for making a mould for an amputated part of a human body.

2. Description of the Related Art

An artificial limb is generally used for an amputee who has had a leg or arm amputated. In production of such artificial limbs, it is necessary to ensure fitness of an artificial limb to the amputated part. Accordingly, the production of an artificial limb starts with making an accurate mould of an amputated part, and followed by the step of carefully making an artificial limb according to the mould. Such mould is made because of the fact that: 1) it takes a long time to make a prosthesis; and 2) an amputee cannot attend throughout the production processes of the prosthesis.

The process of making a mould is as follows. At first, an amputated part and its adjoining part are wound with a gypsum bandage which has not yet hardened, and the outside of the gypsum bandage is kept pressed until the hardening is completed. The hardening of the gypsum bandage takes about 5 or 10 minutes. After being hardened, the gypsum bandage is removed from the body, and is used as a mould or female model to be filled with gypsum. After the hardening of the filled gypsum is completed, the female model is blocked off to thereby produce a male model of the amputated part.

As mentioned above, the making of a female model or mould of an amputated part is the starting point of the production of an artificial limb. Accordingly, the female mould greatly influences the finished quality of an artificial limb as final product. If the mould is poor, the resulting artificial limb dose not only fit the amputee, but may also cause a pain to the amputee. As an amputated part is especially sensitive, much care is required for the making of a mould.

Because an excellent skill is required for making of a mould, it is not easy to obtain a satisfactory mould. For example, the tightness of wound gypsum bandage or the pressure against the gypsum bandage during hardening affects the resulting mould. Moulds made by an immature artisan are usually almost inadequate.

In view thereof, an amputated part holding apparatus 68 using air pressure has been proposed as shown in FIGS. 15A and 15B. Specifically, an amputated part 60 wound with a gypsum bandage 64 is inserted into an inner space 62 defined by a silicone tube 61 having an air chamber 63. Pressurized air is filled in the air chamber 63 to uniformly press the outside of the gypsum bandage 64 during the period of hardening the gypsum bandage 64. The air pressure in the air chamber 63 is numerically controlled by a pressure gauge to regulate the pressure against the outside of the gypsum bandage 64.

Also, an amputated part holding apparatus 69 shown in FIG. 16 is proposed in JSPO Journal, Vol. 14(2), p 178, published by Japanese Society of Prostheses and Orthoses on Apr. 1, 1998. The amputated part holding apparatus 69 includes a hard cylindrical casing 65 and a flexible tube 66 of silicone rubber to define an air chamber 67 therebetween. An inner space is defined by the flexible tube 66. In the amputated part holding apparatus 69, similarly to the amputated part holding apparatus shown in FIG. 16A, pressurized air is filled in the air chamber 67 to press the outside of a gypsum bandage 64 wound on an amputated part 60 which has been inserted in the inner space defined by the flexible tube 66.

These prior art amputated part holding apparatuses 68 and 69 utilize pressurized air to give uniform pressure to the outside of the gypsum bandage, and do not require the high skill. In the case of making a mould of an amputated leg by the above-mentioned amputated part holding apparatuses, however, an amputee is required to seat on a chair. The seated posture is disadvantageous to make a mould of an amputated leg. This is because of the fact that: 1) the amputated part changes in the aspects of shape, bone protrusion, and muscle tension between the standing posture in which the amputated leg receives the body weight of the amputee and the seating posture in which the amputated leg receives no weight; and 2) the prosthesis must work in the standing posture such as walking.

It could be seen that in even these amputated part holding apparatuses 68 or 69, mould making is possible in the standing posture. However, these amputated part holding apparatuses 68 and 69 do not have any support to keep the amputated leg in standing posture. The gypsum bandage is pressed by the pressurized air, but cannot be kept from moving down due to the body weight. To prevent the amputated leg from sinking into the tube, consequently, a support member or device is additionally required to support the body weight of the amputee. However, even if such a support member is provided, actual conditions of the amputated leg cannot be attained, consequently making a mould reflecting a bone protrusion and muscle tension different from the actual standing posture conditions.

It may be possible to hold the body weight by increasing the air pressure in the air chamber. However, such higher pressure changes the shape of the amputated leg and gives undesirable pain to the amputee. This is not adequate for making a mould.

In addition to the above-mentioned prior art apparatuses, another amputated part holding apparatus shown in FIGS. 17A to 17C is proposed in JSPO Journal, Vol. 16(Supplement), p 114-115, published by Japanese Society of Prostheses and Orthoses on Sep. 1, 2000, and PO Academy Journal, Vol. 9(2), p 109-110, published by Japanese Academy of Prosthetists and Orthotists on September, 2001. This amputated part holding apparatus enables mould-making with the body weight being loaded.

This amputated part holding apparatus 70 includes a base member 73, a support channel 72 fixedly mounted on the base member 73, a slider block 74 slidably attached on the support channel 72, and a holder ring 71 fixedly attached on the slidable block 74. An amputated leg to be moulded is inserted into the holder ring 71. The slider block 74 is tightly stayed at a desired position of the support channel 72 by a fastening screw.

The amputated part holding apparatus 70 is used in the following way. At first, a gypsum bandage 64 is wound over an amputated part of a leg 60 in several times. After the gypsum bandage 64 reaches a predetermined hardness, the leg 60 covered with the gypsum bandage 64 is inserted into the holder ring 71, and the body weight is supported by the holder ring 71 until the gypsum bandage 64 attains a predetermined hardness. It should be noted that before applying the body weight, the inner part of the gypsum bandage 64 is required to be moldable. If the inner part of the gypsum bandage 64 should be hardened before applying the body weight, the finished mould has an inner wall not reflecting the actual state of the amputated part in the standing posture. On the other hand, if the outside of the gypsum bandage 64 is not firmly hardened, the gypsum bandage 64 cannot be stayed by the holder ring 71.

Utilizing the nature that the hardening rate of gypsum depends on the temperature, accordingly, gypsum prepared with cold water is used for the inner part 64a of the gypsum bandage 64 and gypsum prepared with hot water is used for the outer part 64b of the gypsum bandage 64 so that the outer part 64b hardens faster than the inner part 64a.

As mentioned above, the apparatuses 68 and 69 need not the excellent skill, but cannot perform molding in the standing posture, and cannot consequently make a good female mould having an inner wall reflecting the conditions of an amputated leg in the standing posture. The apparatus 70 makes it possible to make a female mould having an inner wall reflecting the conditions of an amputated leg in the standing posture, but requires an excellent skill for the operator.

SUMMARY OF THE INVENTION

It is an object of the present invention to provide an amputated part holding apparatus and a mould making method which are free from the problems residing in the prior art.

It is another object of the present invention to provide an amputated part holding apparatus and a mould making method which can make a good mould without the requirement of excellent skill for an artisan.

It is still another object of the present invention to provide an amputated part holding apparatus which makes it possible for an amputee to virtually experience wearing of an artificial limb.

According to an aspect of the invention, a contact member is provided in a casing to define a particle charge chamber between the contact member and the casing. The contact member is operable to come into contact with an amputated part owing to increased particles in the particle charge chamber. The casing is formed with a charging hole for charging particles into the particle charge chamber.

These and other objects, features, aspects, and advantages of the present invention will become more apparent from the following detailed description of the preferred embodiments/examples with reference to the accompanying drawings.

BRIEF DESCRIPTION OF THE DRAWINGS

FIG. 12 is an exploded perspective view showing a particle conveying device provided in the amputated part holding apparatus.

DETAILED DESCRIPTION OF THE PREFERRED EMBODIMENTS

Figure 2:
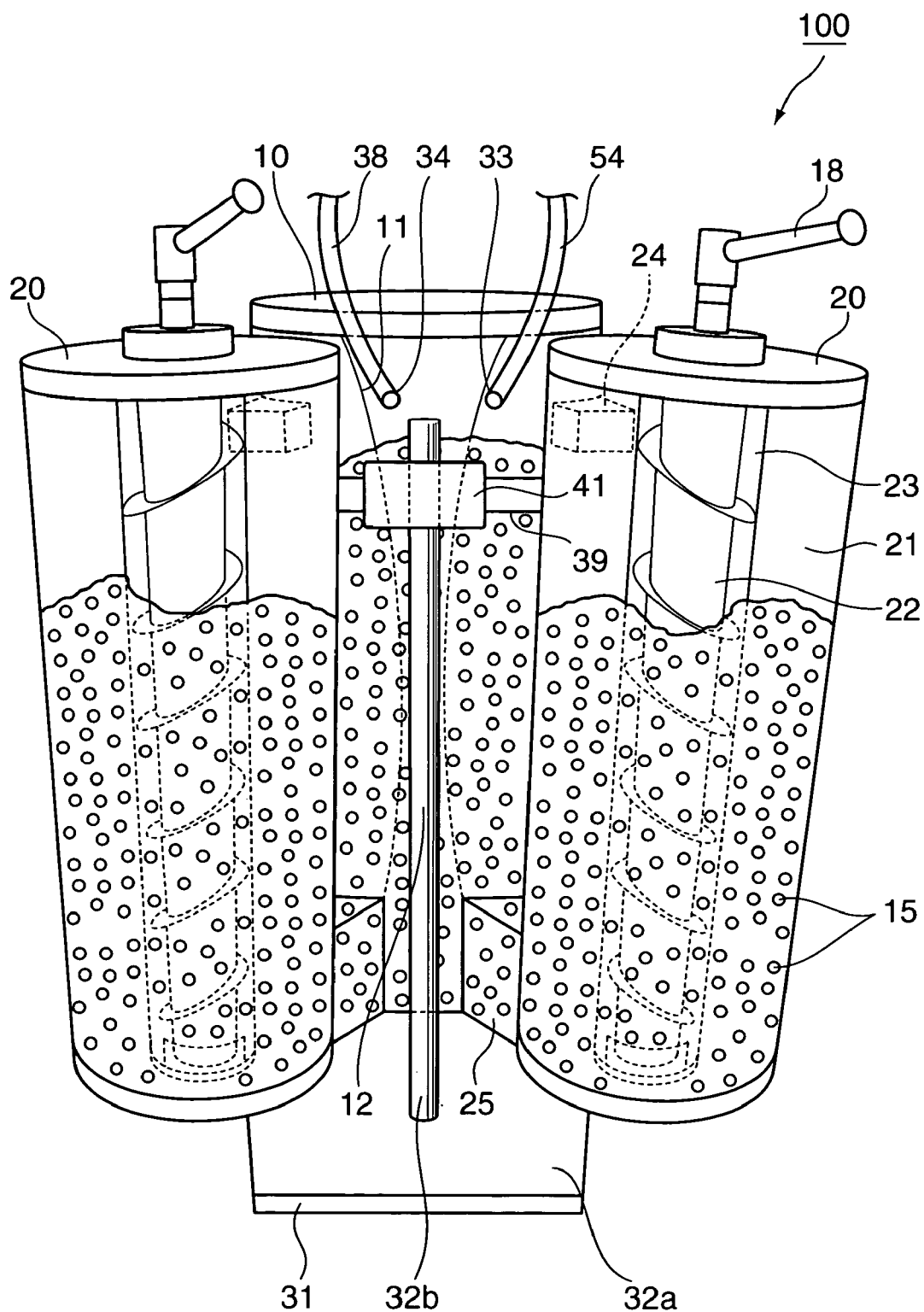
FIG. 2 is a perspective view showing an entirety of the amputated part holding apparatus.
Figure 3:
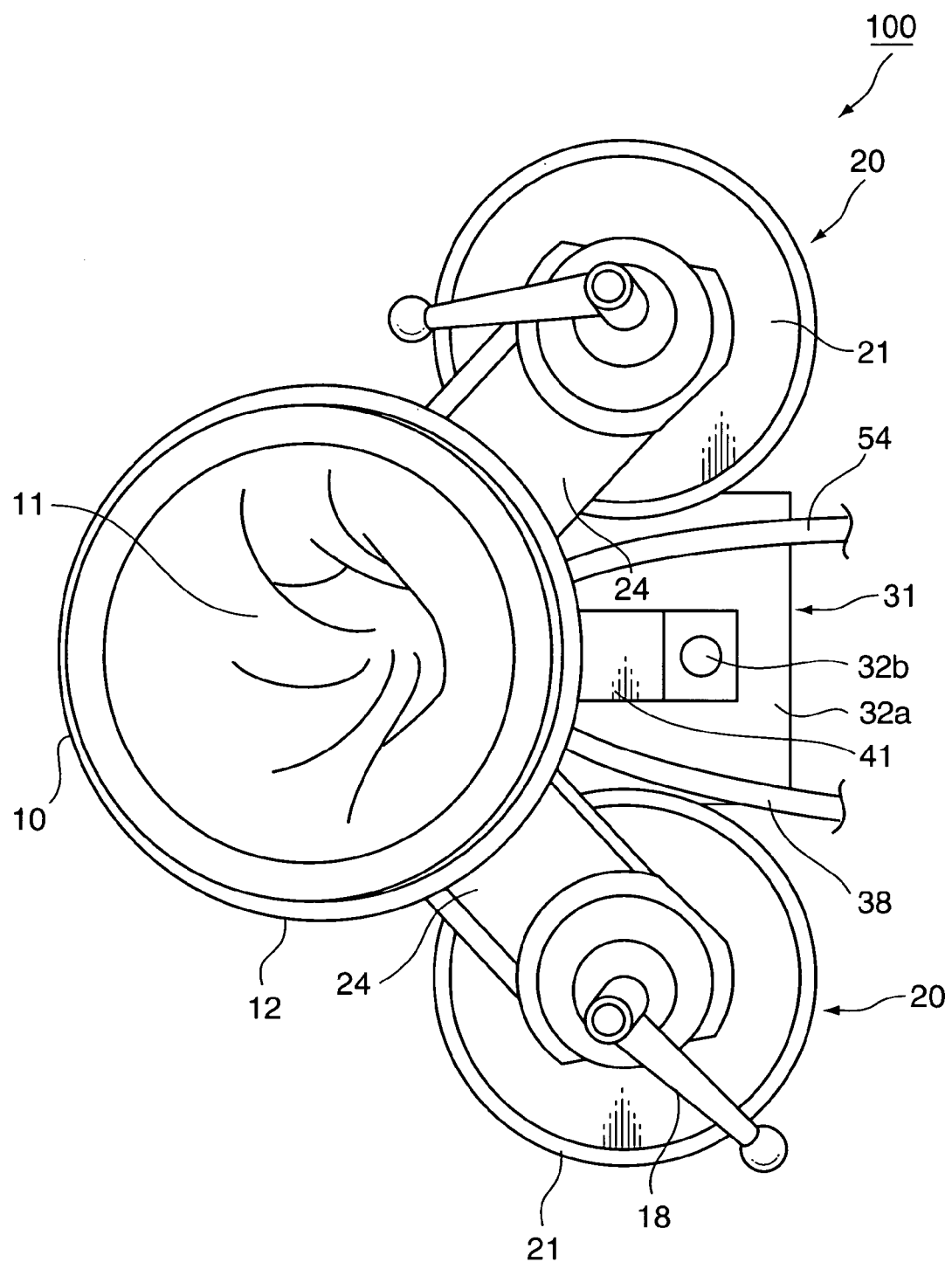
FIG. 3 is a top plane view of the amputated part holding apparatus.
Figure 4:
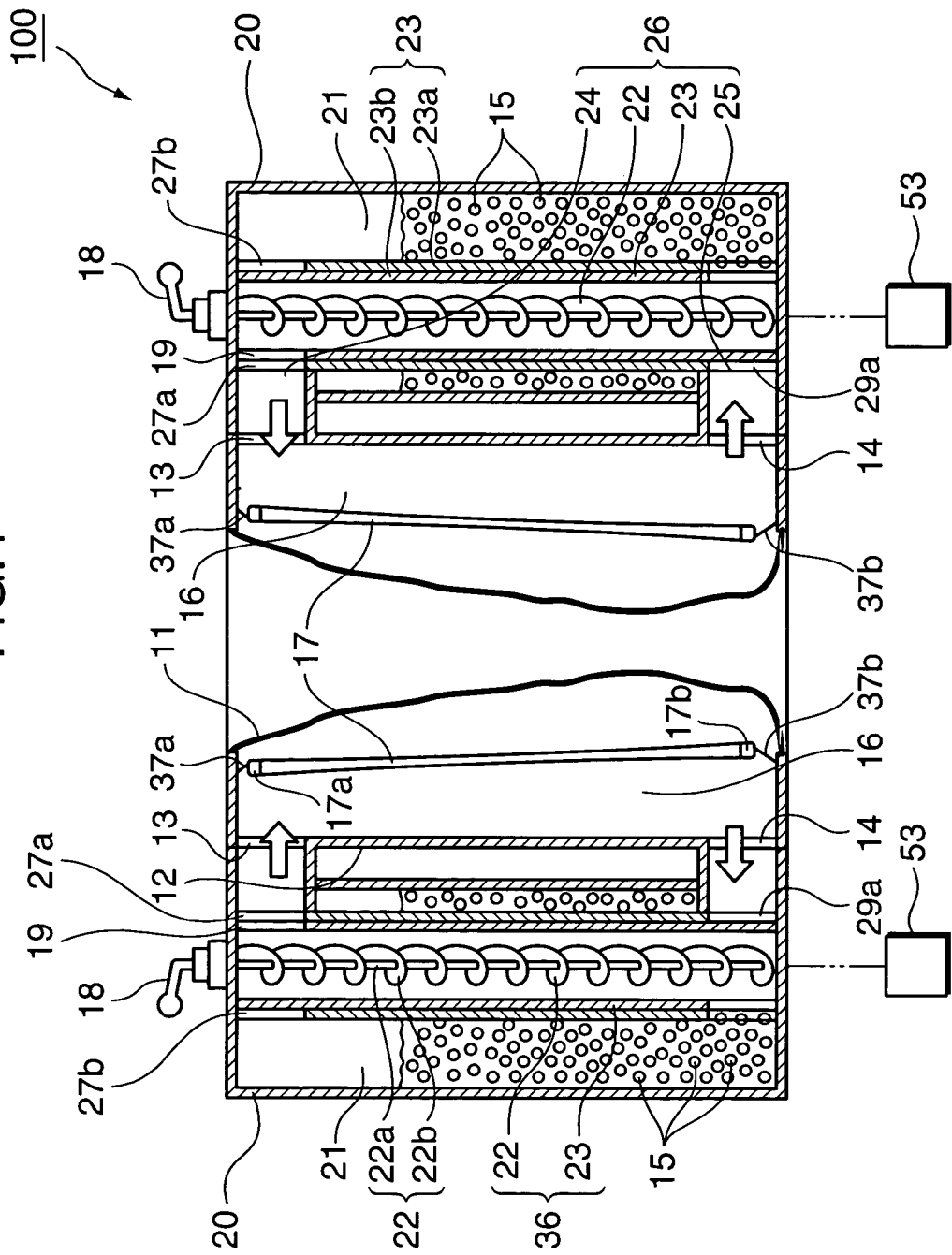
FIG. 4 is a cross-sectional view of the amputated part holding apparatus, showing a state where no leg is inserted.

Referring to FIG. 2, an amputated part holding apparatus 100 embodying the invention is mainly comprised of a holder unit 10, two particle supply units 20, and a support unit 31 for supporting an assembly of the holder unit 10 and the particle supply units 20.

Figure 1:
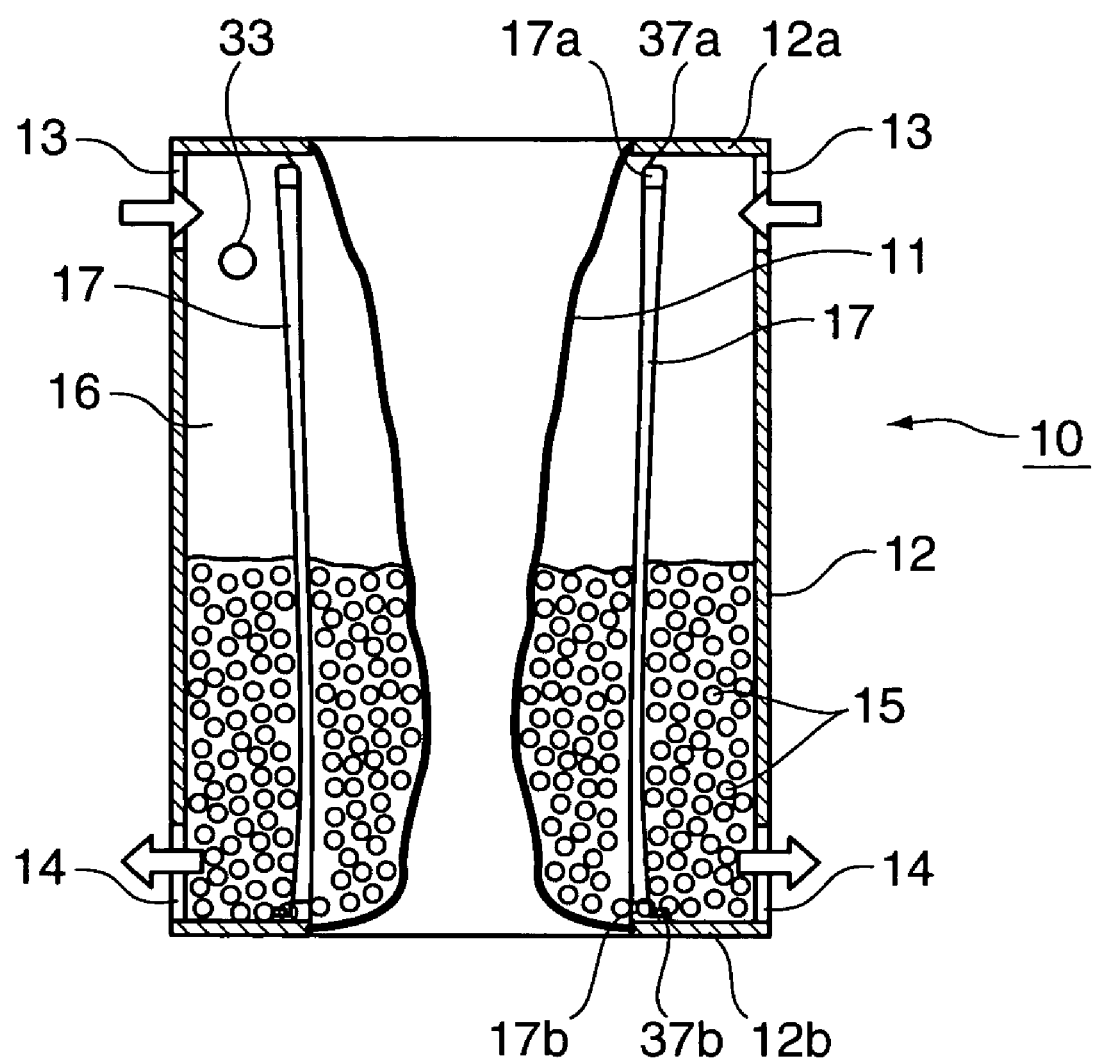
FIG. 1 is a cross-sectional view of a holder unit of an amputated part holding apparatus embodying the invention.

The holder unit 10 includes, as shown in FIG. 1, a cylindrical casing 12 and a contact member 11 provided in the casing 12 in an axial direction thereof. The cylindrical casing 12 and the contact member 11 defines a particle charge chamber 16. In the particle charge chamber 16 is provided four expander members 17 between the contact member 11 and the casing 12.

The casing 12 is formed with a particle charging hole 13 in an upper portion of the casing 12 and a particle discharging hole 14 in a lower portion of the casing 12. Particles 15 are charged into the particle charge chamber 16 through the particle charging hole 13, and discharged from the particle charge chamber 16 through the particle discharging hole 14.

Figure 11A:
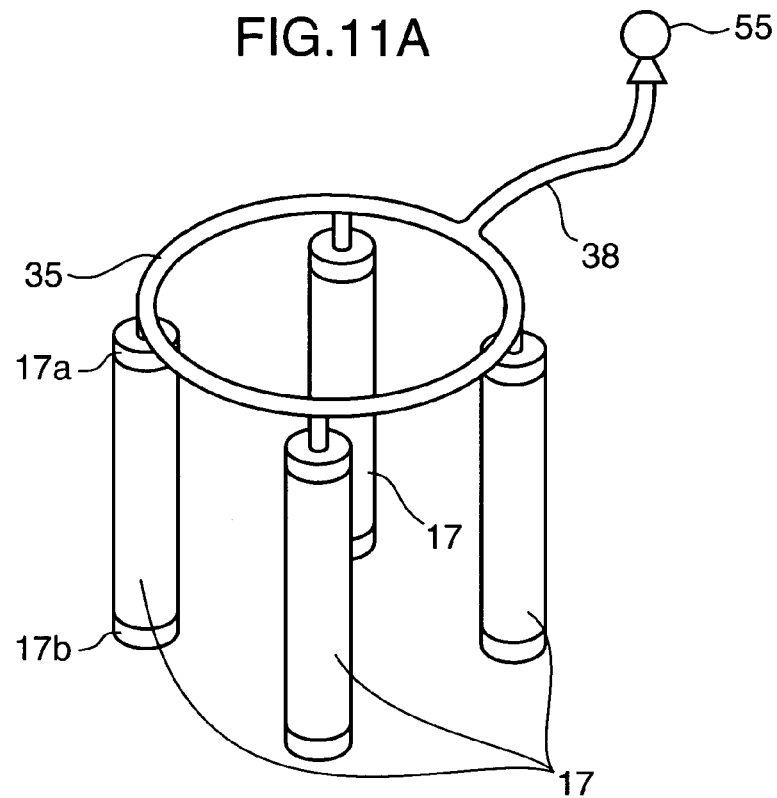
FIG. 11A is a perspective view showing a pressure applying device provided in the amputated part holding apparatus.
Figure 11B:
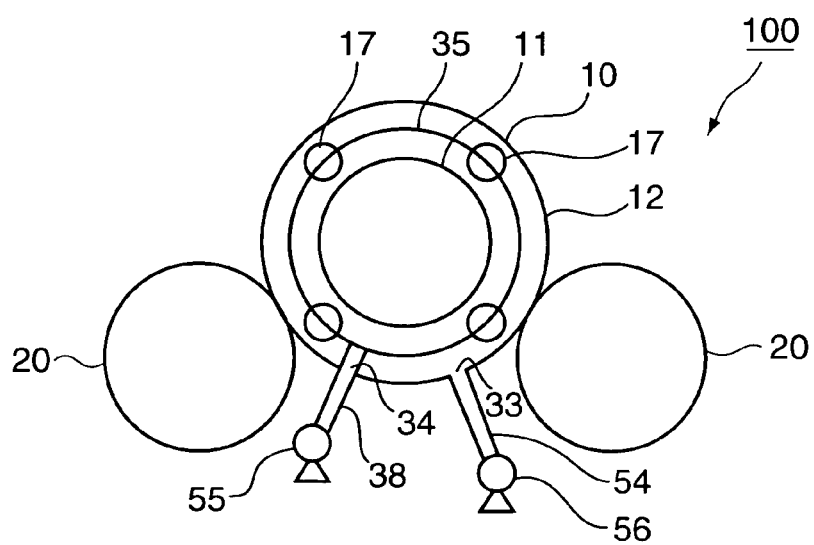
FIG. 11B is a schematic top plan view showing an arrangement of the pressure applying device in the amputated part holding apparatus.

Also, the casing 12 is formed with an air flow hole 33 for supplying pressurized air into the particle charge chamber 16 and drawing pressurized air from the particle charge chamber 16. As shown in FIG. 11B, the air flow hole 33 is connected with an air tube 54 whose end is connected with an air pump 56 to thereby supply or draw out pressurized air into and from the particle charge chamber 16.

Each of the four expander members 17 is in the form of a cylinder, and made of rubber. As shown in FIG. 11A, the four expander members 17 are connected with a tube ring 35 disposed above them. The tube ring 35 is connected with an air pump 55 by a connection tube 38. In this construction, the four expander members 17 are supplied with pressurized air to expand the four expander members 17 simultaneously.

Each expander member 17 is attached on the cylindrical casing 12 by fastening a top portion 17a of the expander member 17 on a top inner wall of the cylindrical casing 12 by a string 37a, and attaching a bottom portion 17b of the expander member 17 on a bottom inner wall of the cylinder casing 12 by a screw 37b. In this way, the expander member 17 is held in a vertical posture. The volume of each expander member 17 is increased or decreased by supplying or drawing pressurized air into and from the expander member 17. The supplied pressurized air applies pressing forces to the particles 15 charged in the particle charge chamber 16. The expander members 17 and the air pump constitute a pressure applying device.

The particles 15 are made of synthetic resin, and have the shape of balls having an averaged diameter of 6 mm. The particles 15 are solid. The contact member 11 is made of silicone rubber, and has a good flexibility and expandability. The casing 12 is made of a material having enough strength to resist the above-applied pressure.

Each particle supply unit 20 is provided with a particle storage container casing 21 and a particle conveying device 26. The particle conveying device 26 is comprised of an outer cylinder 23a, an inner cylinder 23b, and a conveying screw 22 provided in the inner cylinder 23b, a charging passage 24, and a discharging passage 25.

Referring to FIG. 12, the outer cylinder 23a is formed with an upper charging opening 27a and an upper discharging opening 27b in an upper portion thereof, and a lower discharging opening 29a and a lower charging opening 29b in a lower portion thereof. The upper charging and discharging openings 27a and 27b, the lower discharging and charging openings 29a and 29 are in the opposite directions. These openings 27a, 27b, 29a, and 29b each have a circumferential length corresponding to a circumference angle of 90 degrees. The outer cylinder 23a is fixedly mounted on a top inner surface and a bottom inner surface of the casing 21.

The charging passage 24 connects the particle charging hole 13 of the casing 12 with the upper charging opening 27a of the outer cylinder 23a, and the discharging passage 25 connects the particle discharging hole 14 of the casing 12 with the lower discharging opening 29a of the outer cylinder 23a.

The inner cylinder 23b is formed with an upper hole 19 in an upper portion thereof and a lower hole 28 in a lower portion thereof. The upper hole 19 and the lower hole 28 are formed in the opposite directions. The circumferential length of the upper and lower holes 19 and 28 is the same as or smaller than the circumferential length of the openings 27a, 27b, 29a, and 29b of the outer cylinder 23a. The inner cylinder 23b is rotatably placed in the outer cylinder 23a. The inner cylinder 23 is fixedly attached with a handle 18 to thereby rotate the inner cylinder 23.

When charging particles 15 into the particle charge chamber 16 from the storage chamber 20a of the particle supply unit 20, the inner cylinder 23b is placed in such a position that the upper hole 19 agrees with the upper charging opening 27a, and the lower hole 28 agrees with the lower charging opening 29b, and the upper discharging opening 27b and the lower discharging opening 29a are closed by the wall of the inner cylinder 23b.

When discharging particles 15 from the particle charge chamber 16 to the storage chamber 20a, the inner cylinder 23b is placed in such a position that the upper hole 19 agrees with the upper discharging opening 27b, and the lower hole 28 agrees with the lower discharging opening 29a, and the upper charging opening 27a and the lower charging opening 29b are closed by the wall of the inner cylinder 23b.

When the particle charge chamber 16 is applied with pressure, the inner cylinder 23b is placed in such a position that the charging passage 24 and the discharging passage 25 are closed by the wall of the inner cylinder 23b.

Figure 13:
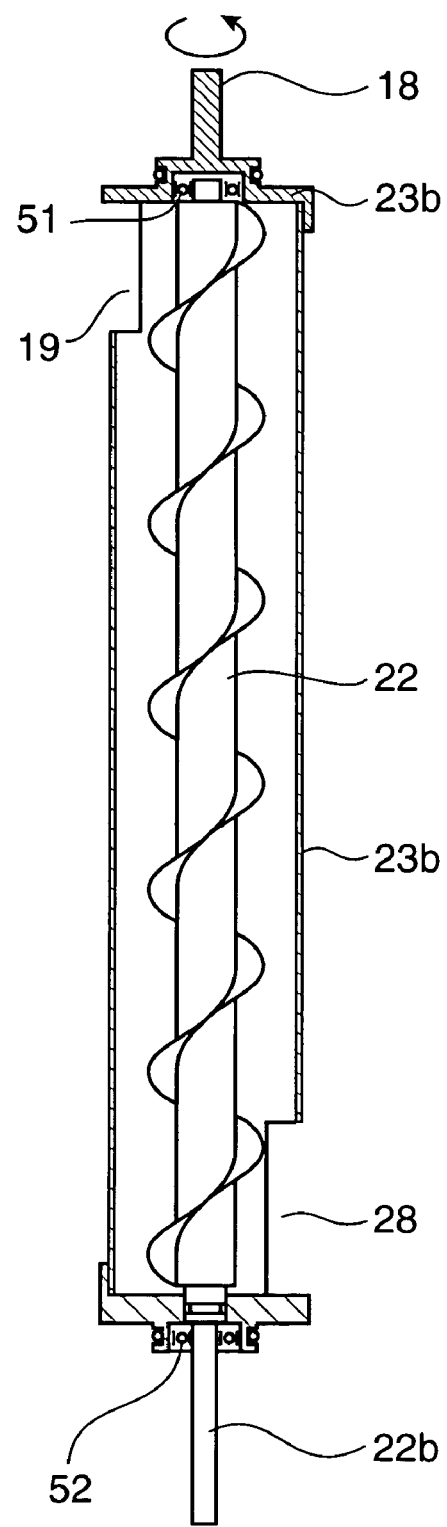
FIG. 13 is a cross-sectional view of the particle conveying device.

Referring to FIG. 13, the conveying screw 22 having a spiral blade 22a is rotatably mounted in the inner cylinder 23b. Specifically, a top end of the conveying screw 22 is supported in an upper wall of the inner cylinder 23b by way of a bearing 51 and a bottom end of the conveying screw 22 is supported in a hole formed in a bottom wall of the container casing 21 by way of a ball bearing 52. The conveying screw 22 has an extension shaft 22b which is mechanically connected with a direct current driving motor 53. The conveying screw 22 is driven to convey particles 15 from the lower hole 28 to the upper hole 19.

Figure 14A:
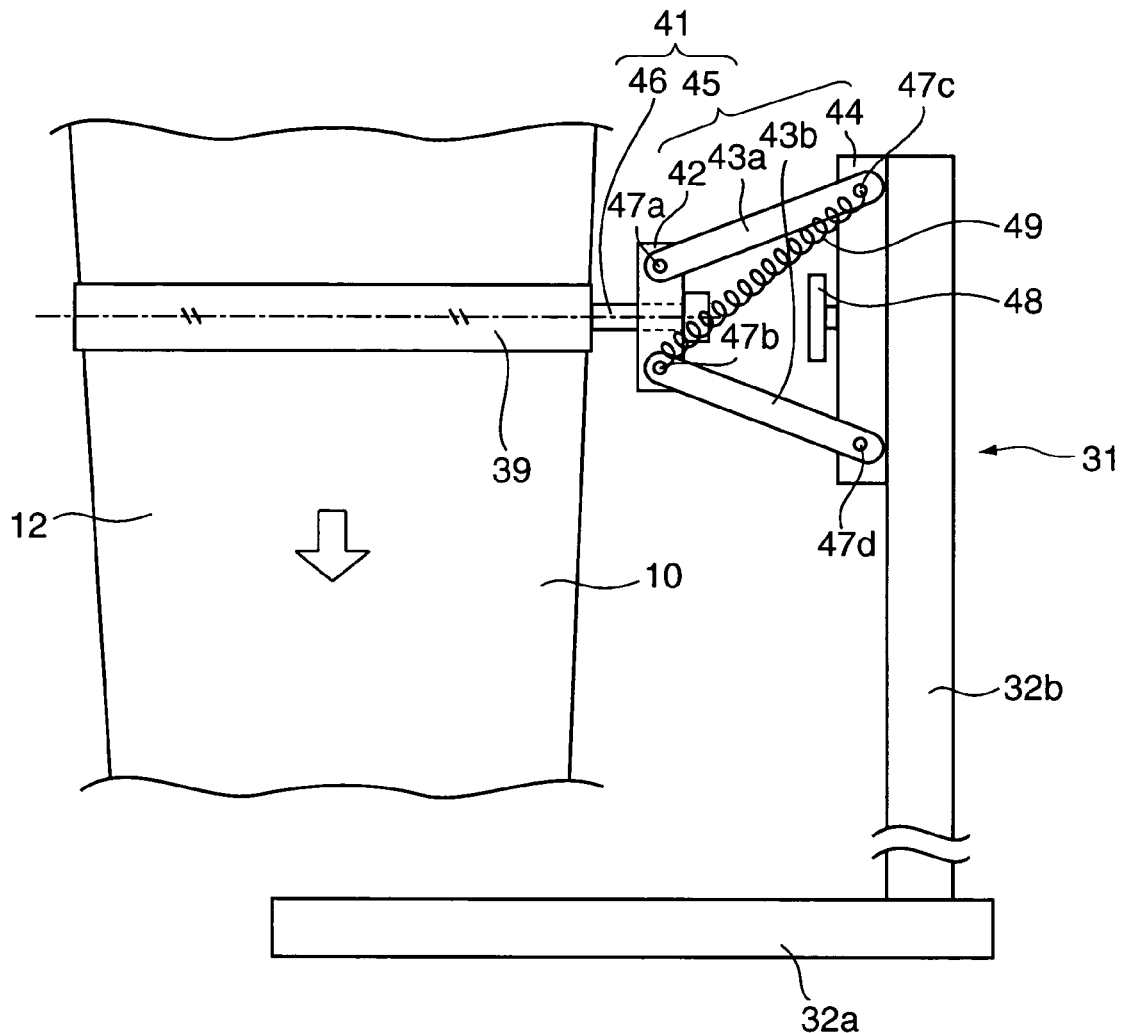
FIG. 14A is a side elevation view of a support unit of the amputated part holding apparatus.
Figure 14B:
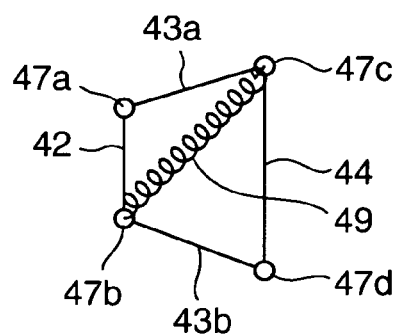
FIG. 14B is a schematic diagram showing a four-link mechanism provided on the support unit.
Figure 15A:
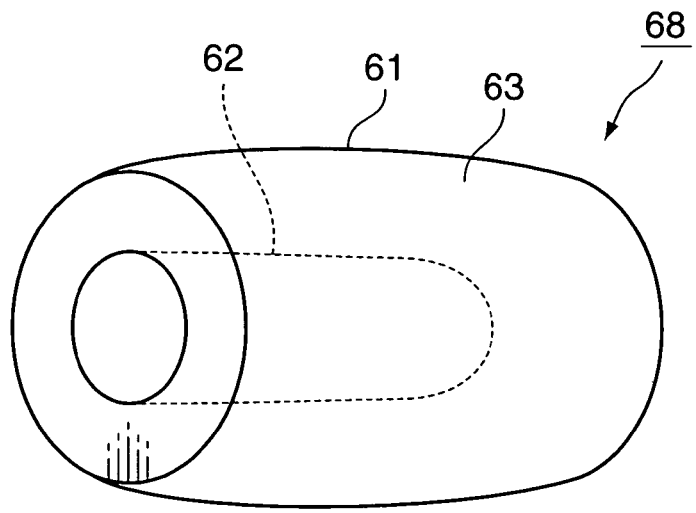
FIG. 15A is a perspective view of a prior art amputated part holding apparatus.
Figure 15B:
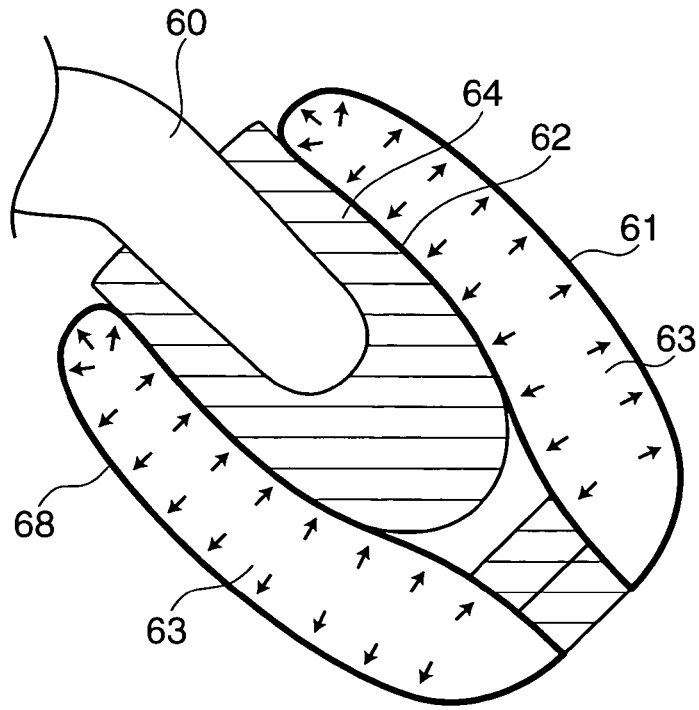
FIG. 15B is a sectional view of the amputated part holding apparatus shown in FIG. 15A.
Figure 16:
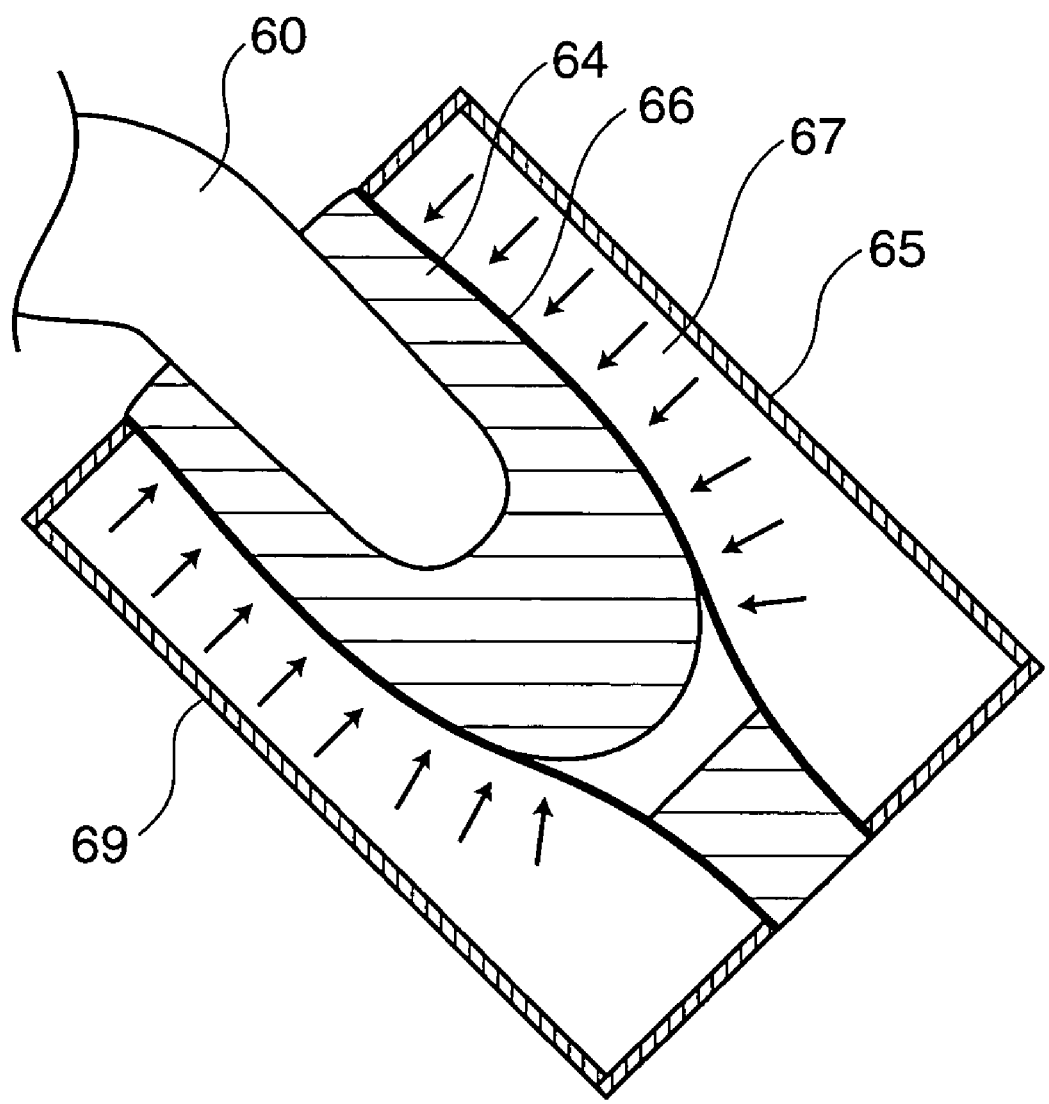
FIG. 16 is a cross-sectional view of another prior art amputated part holding apparatus.
Figure 17B:
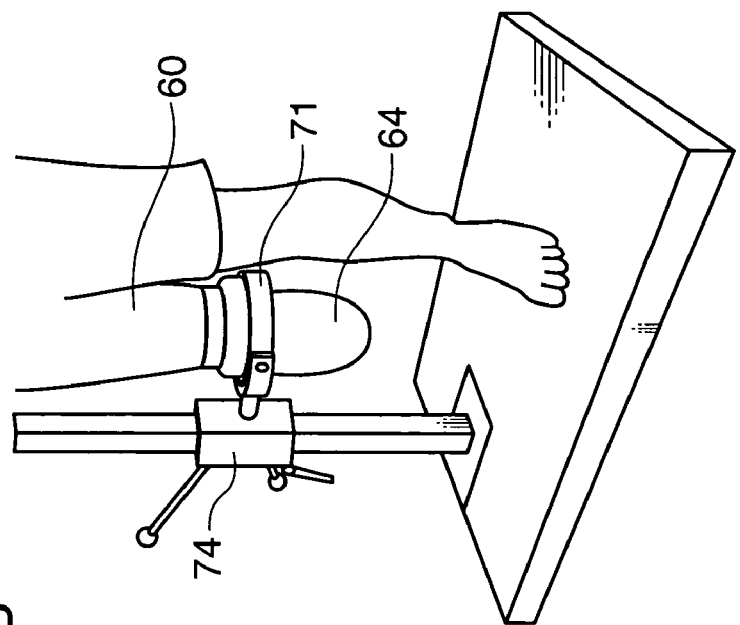
FIG. 17B is a perspective view of the amputated part holding apparatus shown in FIG. 17A, showing a state of supporting an amputated leg.
Figure 17C:
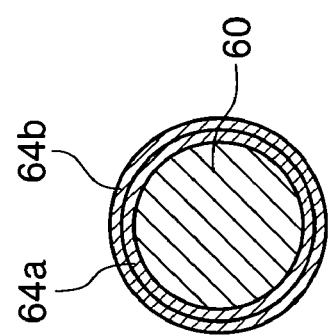
FIG. 17C is a cross-sectional view of the amputated leg wearing gypsum bandage.
Figure 17A:
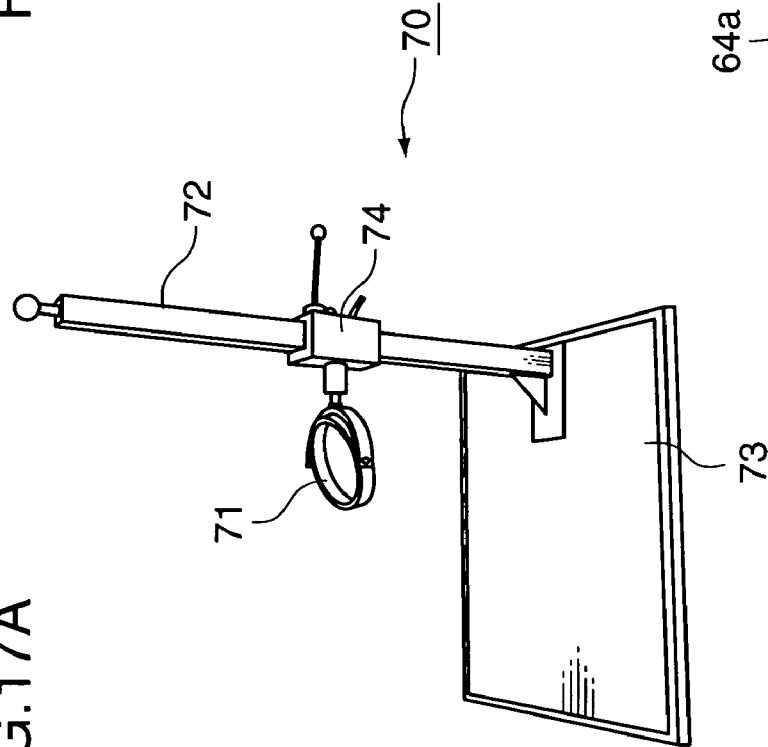
FIG. 17A is a perspective view of still another amputated part holding apparatus.

The holder unit 10 and the particle supply units 20 are integrally mounted on the support unit 31 as shown in FIGS. 14A and 14B. The support unit 31 is constructed by a base plate 32a, a support pole 32b, a support angle regulator device 41, and a holding ring 39. The holding ring 39 holds the casing 12 of the holder unit 10.

The support angle regulator device 41 includes a pivot shaft 46 and a four-link mechanism 45. The pivot shaft 41 fixedly supports the holding ring 39, and is adapted for rotating the holding ring 39 about a horizontal axis, and the four-link mechanism 45 is adapted for inclining a vertical axis of the holding ring 39 with respect to the support pole 32b.

The four-link mechanism 45 includes a movable member 42, an upper arm member 43a, a lower arm member 43b, and an attachment member 44. The upper and lower arm members 43a and 43b are pivotally connected with the movable member 42 and the attachment member 44 by pins 47a, 47b, 47c, and 47d. The movable member 42 rotatably supports the pivot shaft 46 supporting the holding ring 39. The attachment member 44 is slidably mounted on the support pole 32b. The attachment member 44 is moved to a desired position of the support pole 32b, and is firmly held at the position of the support pole 32b by a fastening member 48. Further, it may be preferable to provide a spring 49 between the opposite pins 47b and 47c to prevent the arm member 43b from rotating uncontrollably due to the weight of holder unit 10 and the supply units 20.

Next will be described a method of making a mould of an amputated part using the amputated part holding apparatus 100 shown in FIG. 2.

At first, a gypsum bandage 64 which has not yet been hardened is wound on an amputated part of a leg 60. If necessary, an enclosing cloth cover may be placed over the amputated part to keep the skin from coming into direct contact with the gypsum bandage 64, and a synthetic film may be further wound over the skin or the enclosing cloth cover to prevent gypsum from adhering to the skin.

The amputated leg 60 covered with the gypsum bandage 64 is inserted into a space defined by the contact member 11 of the amputated part holding apparatus 100. Further, it may be preferable to wrap the outside of the gypsum bandage 64 by a synthetic film to ensure easy withdrawal from the contact member 11 after the gypsum bandage 64 is hardened.

Figure 5:
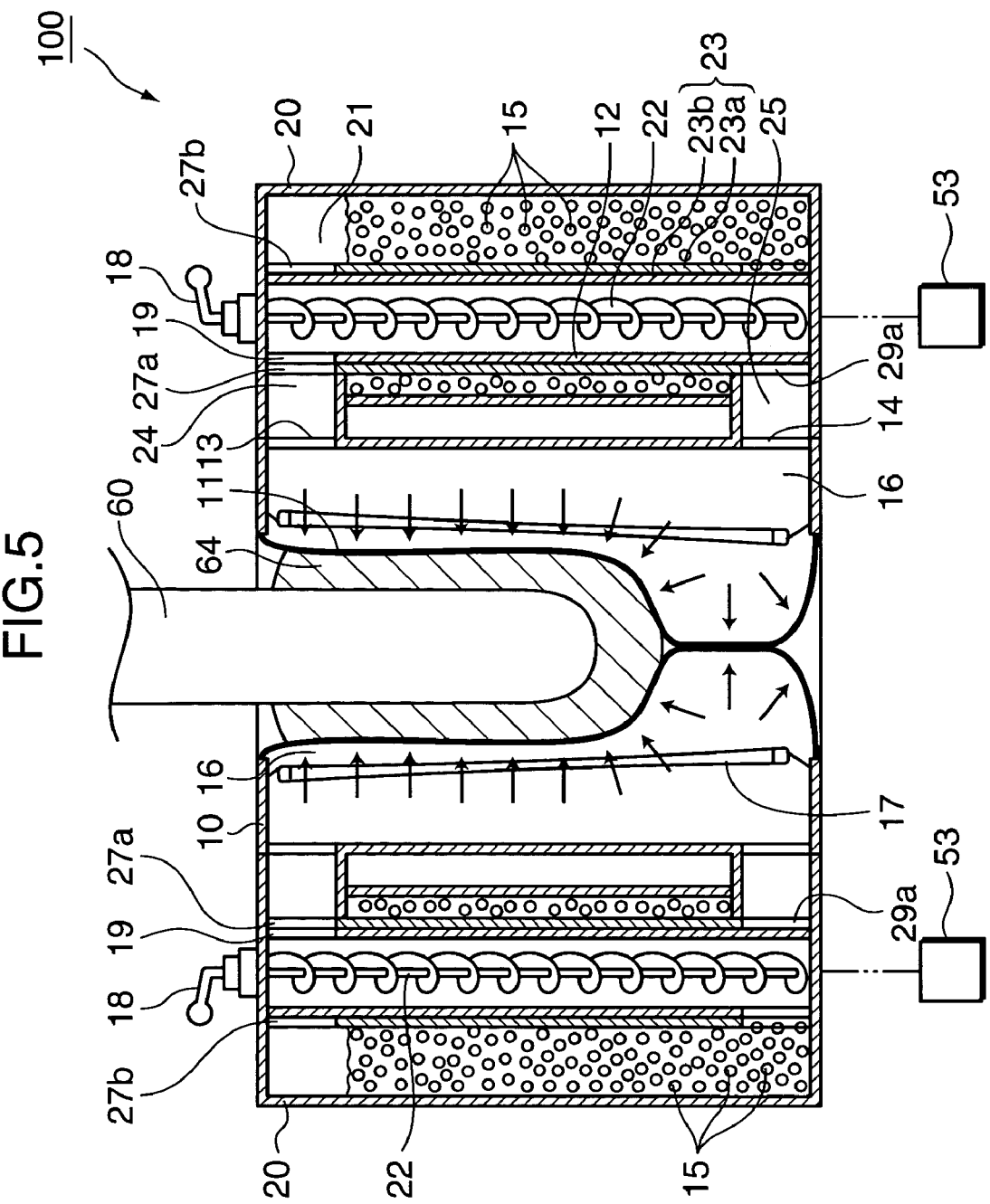
FIG. 5 is a cross-sectional view of the amputated part holding apparatus, showing a state where an amputated leg wearing a gypsum bandage is inserted.
Figure 6:
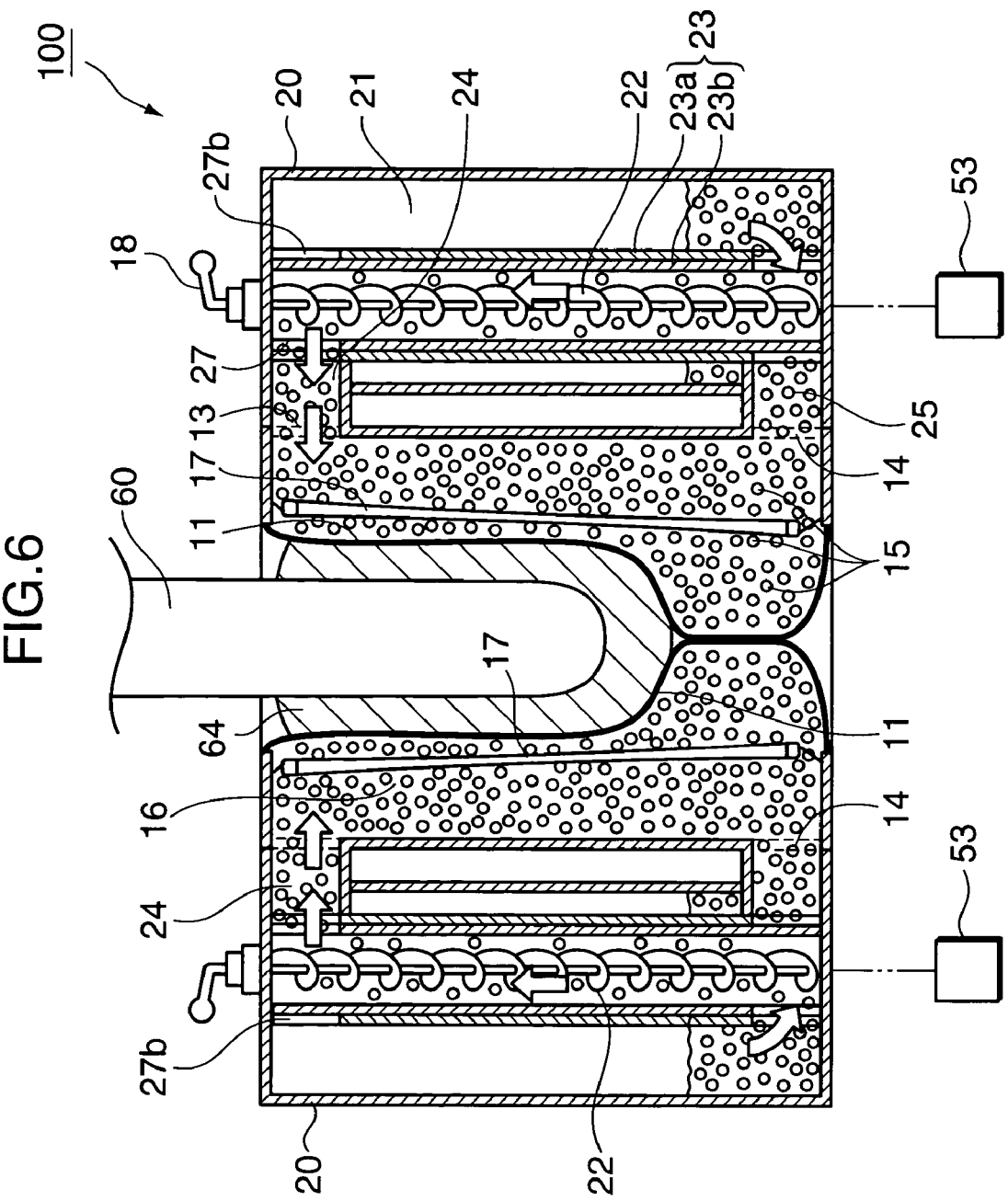
FIG. 6 is a cross-sectional view of the amputated part holding apparatus, showing a state where particles are being charged.

As shown in FIG. 5, subsequently, pressurized air is supplied into the particle charge chamber 16 to cause the contact member 11 to come into contact with the gypsum bandage 64 by driving the pump 56. Thereafter, the conveyor screw 22 is driven by the motor 53 to charge particles 15 into the particle charge chamber 16 from the storage chamber 20a through the lower charging opening 29b of the outer cylinder 23a and the lower hole 28 of the inner cylinder 23b in which the conveyor screw 22 is being driven, the upper hole 19 of the inner cylinder 23b and the upper charging opening 27a, the charging passage 24, and the particle charging hole 13 as shown in FIG. 6. In this time, the upper and lower discharging opening 27b and 29a are closed.

Figure 7:
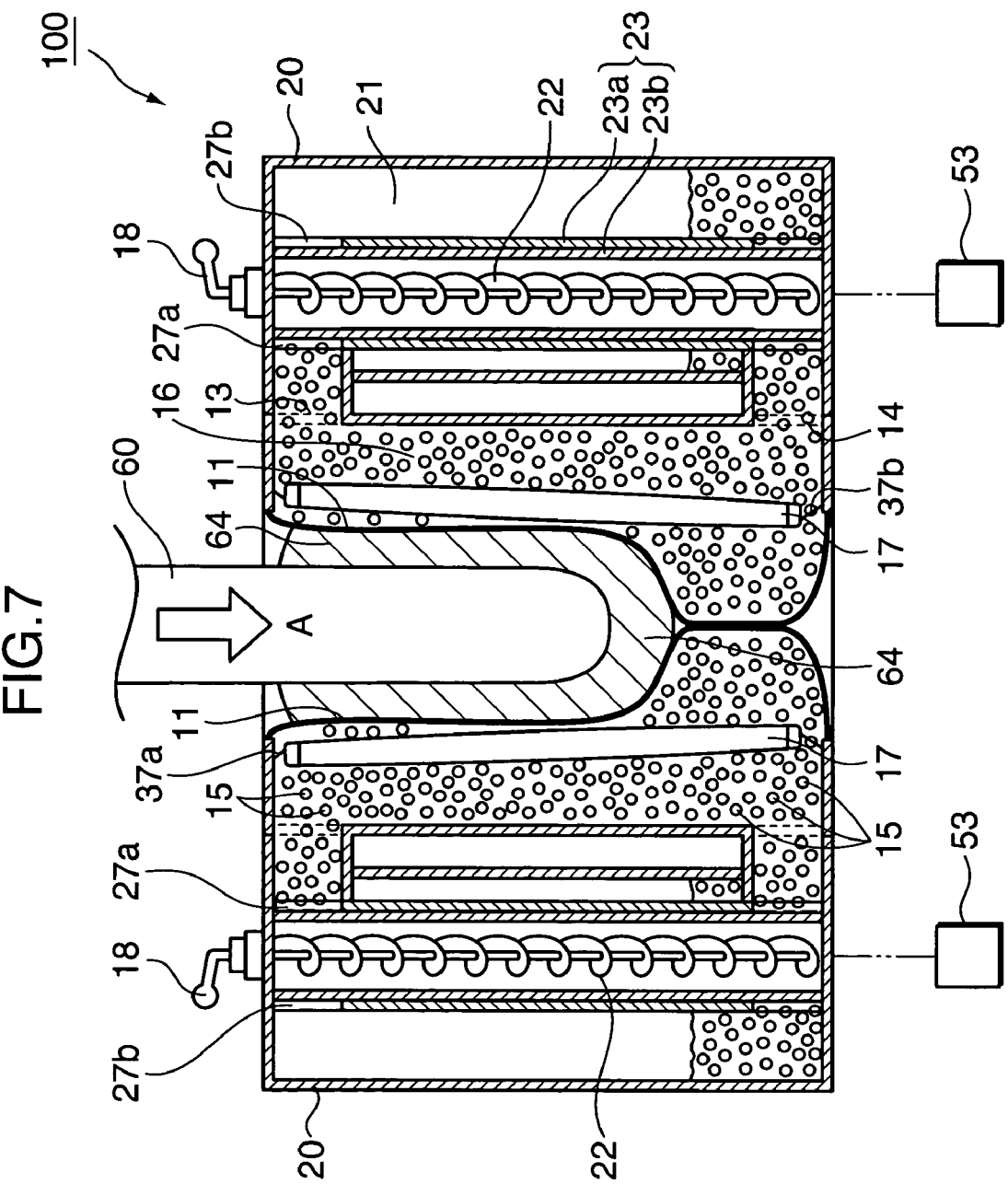
FIG. 7 is a cross-sectional view of the amputated part holding apparatus, showing a state where the particles are held immovable.

When the particle charge chamber 16 is filled with particles 15, the charging of particles 15 is stopped, and the particle charging hole 13 is closed to seal up the particle charge chamber 16. Thereafter, the expander members 17 are inflated by air to apply pressing forces to the particles 15 in the particle charge chamber 16 by driving the pump 55, so that the particles 15 in the particle charge chamber 16 are tightly and immovably pressed against one another within the limited space as shown in FIG. 7. It should be noted that particles having some flexibility are preferably used to increase the immovability of the particles 15 because the particles 15 are likely to deform owing to the high pressing forces. However, the use of particles having undesirably high flexibility should be carefully avoided to prevent the situation that only particles near the expander members 17 deform and the pressing forces are not consequently transmitted to the other particles.

Next, the amputee is allowed to take the standing position to load his/her weight onto the gypsum bandage 64. The standing position is held until the gypsum bandage 64 reaches the predetermined hardness. In this way, the gypsum bandage 64 receives the shape of the amputated part under the standing condition.

The particle charge chamber 16 is adequately supplied with pressurized air during the periods of charging particles and hardening of the gypsum bandage 64 to thereby press the outside of the gypsum bandage 64 uniformly. The uniform pressing of the gypsum bandage 64 can be accomplished without connection with the skill of artisan. Since the particle charge chamber 16 is filled with the particles 15, there is no likelihood that the leg 60 wearing the gypsum bandage 64 sinks in the contact member 11 when the leg loads the weight in the direction of the arrow A in FIG. 7. When the particles is movable and in a state of loose packing, the leg 60 sinks down and pushes the particles 15 away. In this case, however, the particles 15 are tightly packed and immobilized, and can take tight hold of the body weight.

Figure 8:
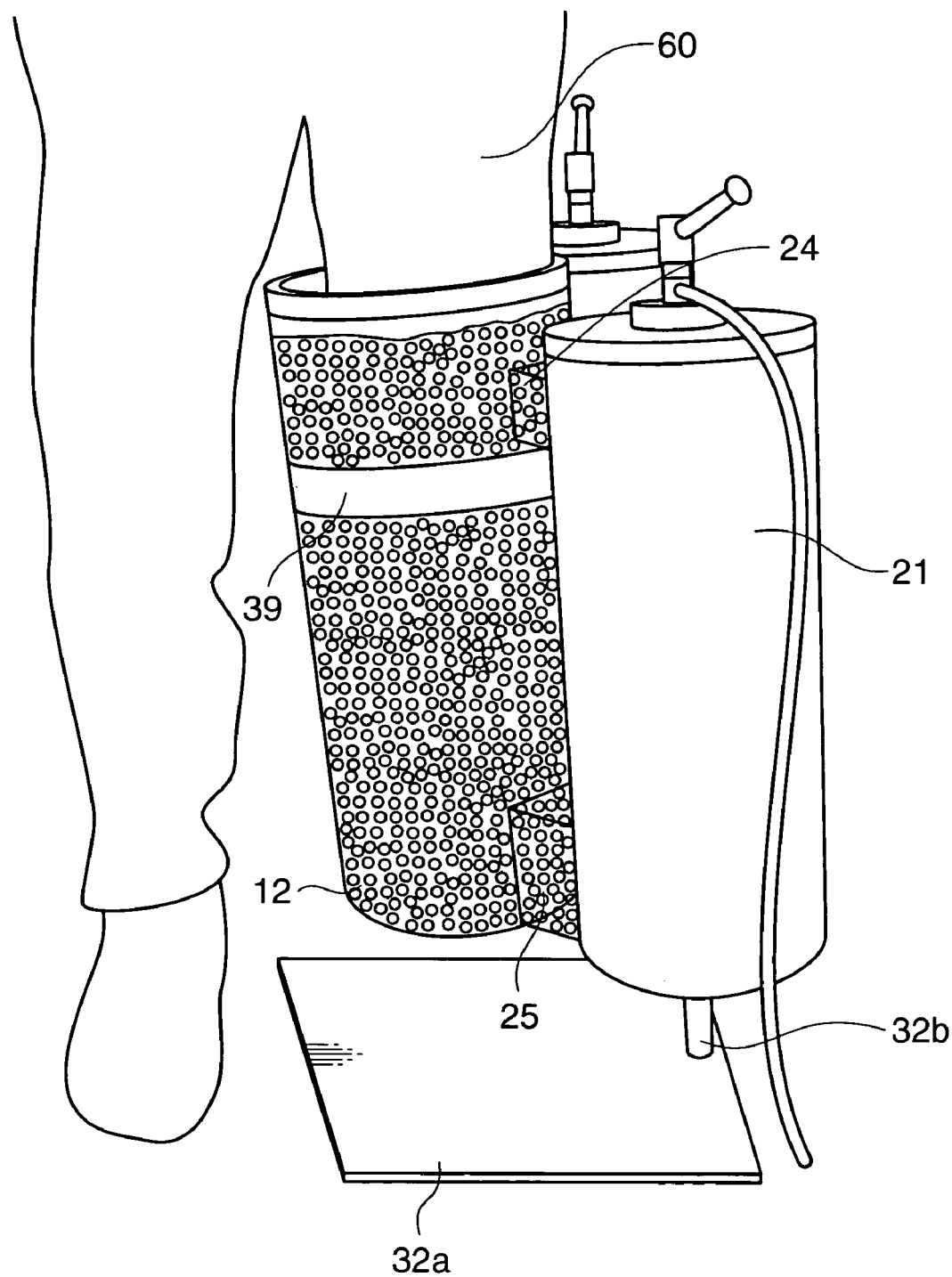
FIG. 8 is a perspective view of the amputated part holding apparatus, showing a state of allowing the gypsum bandage to be hardened.

FIG. 8 shows the state of waiting for hardening of the gypsum bandage 64. The casing 12 of the holder unit 10 is inserted in the holding ring 39 of the support unit 31 together with the particle supply units 20. In the insertion, the holding ring 39 is pivotable about the horizontal axis and inclinable with respect to the support pole 32a. Accordingly, even if the insertion angle of the amputated leg 60 deviates from the predetermined angle, the casing 12 of the holder unit 10 can be set in a position suitable for the person carrying the units 10 and 20 easily.

Figure 9:
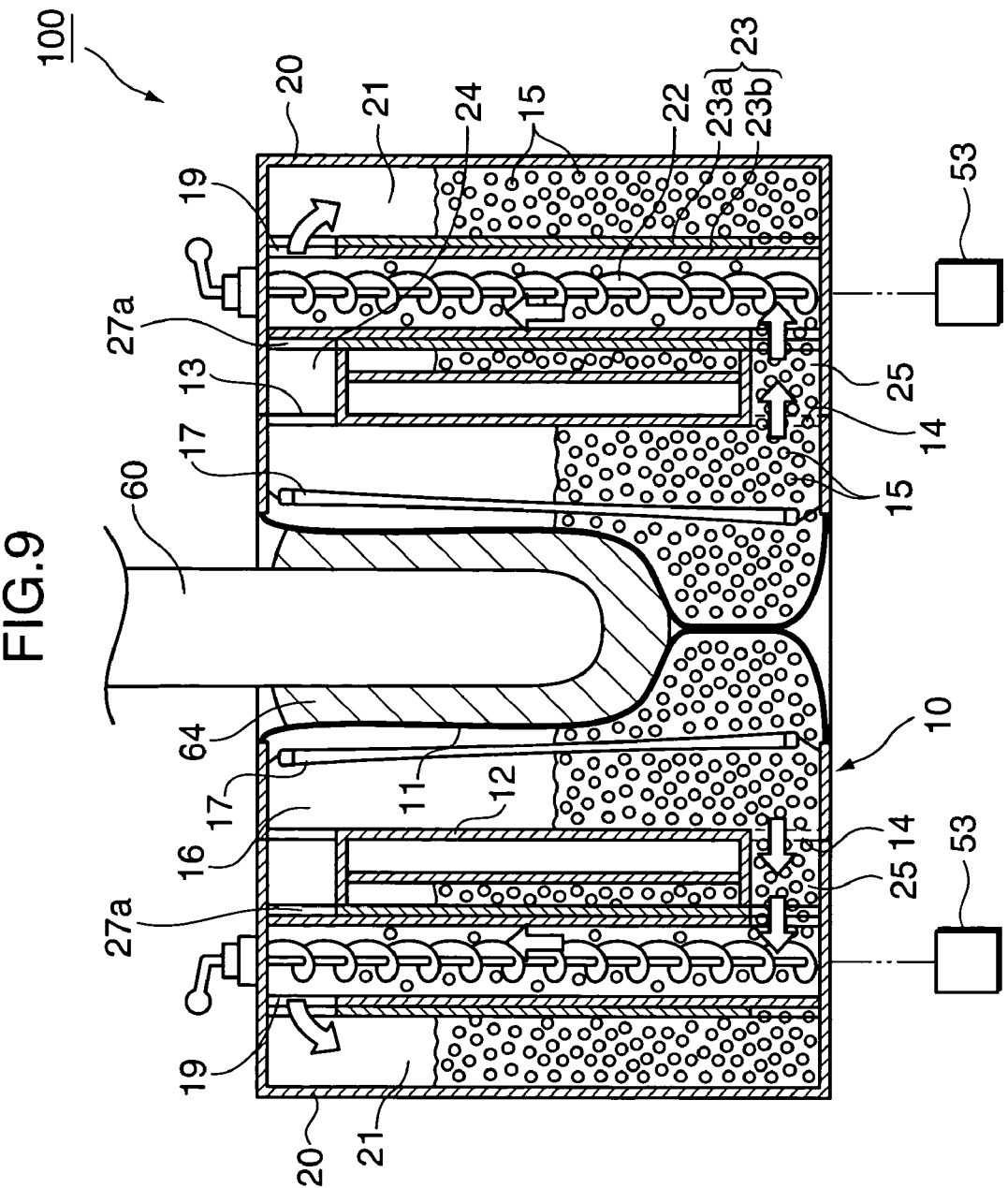
FIG. 9 is a cross-sectional view of the amputated part holding apparatus, showing a state where particles are being discharged.

After the gypsum bandage 64 is completely hardened, as shown in FIG. 9, the expander members 17 are deflated, and the particle discharging hole 14, the lower and upper discharging openings 29a and 27b are opened while the upper and lower charging opening 27a and 29b are closed to discharge particles 15 from the particle charge chamber 16 into the storage chamber 20a through the discharging passage 25 and the inner cylinder 23b in which the conveyor screw 22 is being driven.

Figure 10:
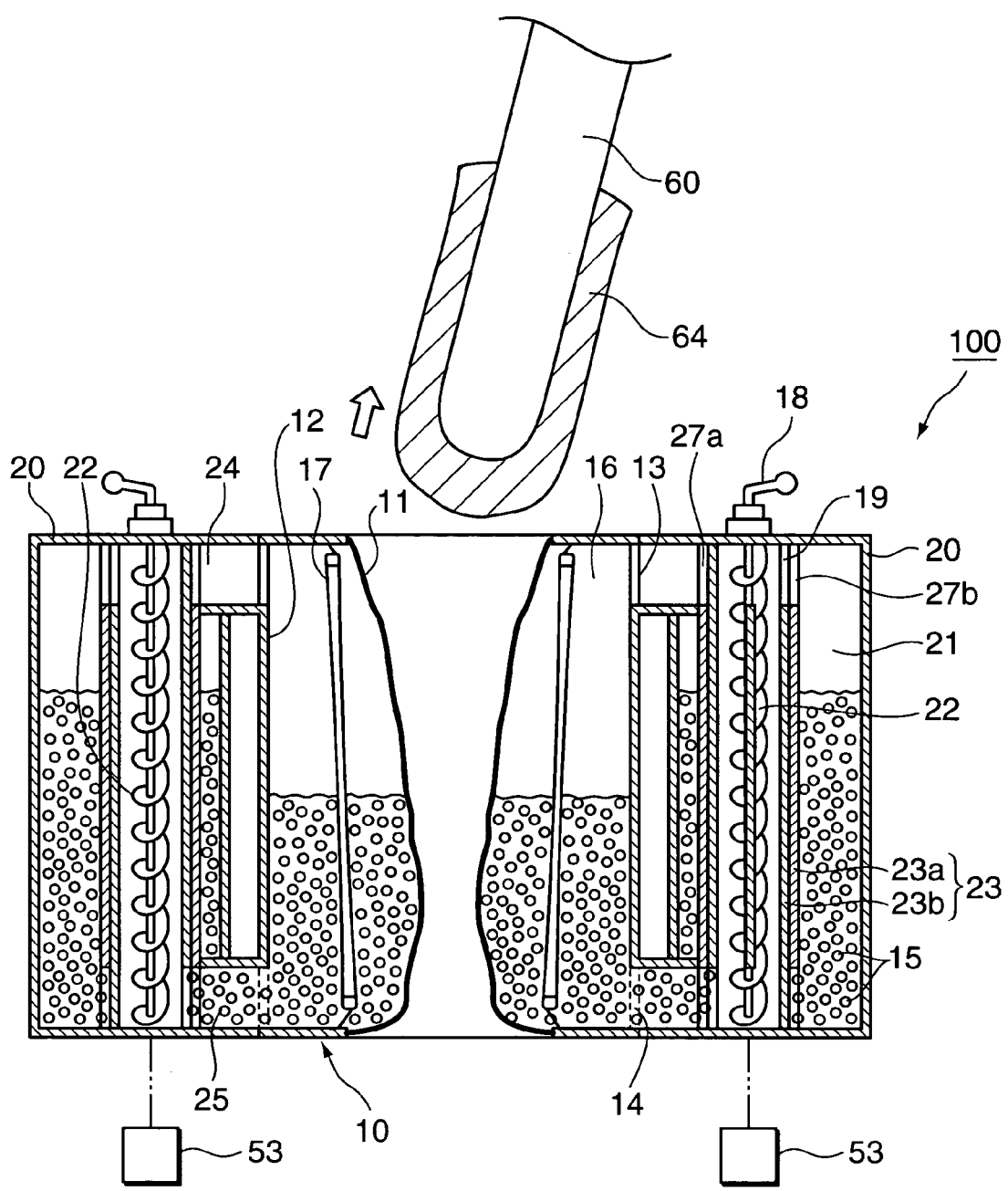
FIG. 10 is a cross-sectional view of the amputated part holding apparatus, showing a state where the amputated leg wearing the gypsum bandage is withdrawn out of the apparatus.

As mentioned above, the particles 15 are discharged together with the pressurized air from the particle charge chamber 16, consequently reducing the pressure onto the gypsum bandage 64 to ensure easy withdrawal of the leg 60 wearing the gypsum bandage 64 as shown in FIG. 10.

Finally, the gypsum bandage 64 is removed from the leg 60 to complete making of a mould or female model.

In this way, using the amputated part holding apparatus provided with the particle suppliers enables making of a good mould reflecting the actual state of an amputated part in the standing posture without the excellent skill.

Further, the amputated part holding apparatus can provide a virtual experience of wearing an artificial limb on an amputated part. The virtual experience is accomplished in the similar way to the above-mentioned mould making except for wearing no gypsum bandage.

Specifically, an amputated part of a leg 60 on which a cloth cover is put is inserted into the contact member 11 of the amputated part holding apparatus, and the particle charge chamber 16 is supplied with pressurized air to cause the contact member 11 to come into contact with the leg 60, and particles 15 are charged into the particle charge chamber 16, and the expander members 17 are inflated to apply pressing forces to the particles 15 to thereby make the particles 15 immovable.

In this way, the amputated leg 60 is firmly supported by the holding apparatus even when the person stands. The person can virtually experience the condition or state of standing with wearing an artificial limb. Also, the holding apparatus can used as a training machine for a person having an amputated part until an artificial limb is actually finished. The apparatus is useful for an person having an amputated leg to perform standing training.

It should be noted that this invention is not limited to the foregoing embodiments, but may be changed into desired modifications.

In the foregoing embodiment, for example, the spherical particles 15 are used, However, the shape of particles is not limited to a sphere, but may be a non-spherical. The non-spherical shape is advantageous in accomplishing immovable and tight pack. The use of non-spherical particles enables accomplishment of immovable state of particles without such as additional pressing member as the expander member 17. However, the non-spherical particles are disadvantageous for the convey using the screw 22.

Further, the size of particles is not limited to the diameter of 6mm as aforementioned. Particles larger or smaller than 6mm may be used. However, particles smaller than the gap between the conveying screw 22 and the inner cylinder 23b are not preferable because there is a likelihood that particles come into the gap and consequently hindering the convey of particles. On the other hand, exceedingly large particles are not good because there is a likelihood that the shape of particles are impressed in an outside surface of the gypsum bandage. In view thereof, it is preferable to use particle having a diameter of 3 mm to 6 mm.

In the foregoing embodiment, the solid particles are used. However, it may be possible to use particles having a closed space. The particles having a closed space are preferable because they are easily handled owing to lighter weight and they can be filled more compactly owing to higher flexibility.

In the foregoing embodiment, the particle conveying device includes the outer cylinder 23a and the inner cylinder 23b. However, it may be possible to use only the inner cylinder or a single cylinder 23b without the outer cylinder 23a to change over the charging and the discharging. Specifically, the charging passage 24 and the discharging passage 25 are extended onto the cylinder 23b. When charging particles 15, the cylinder 23b is placed in such a position that the upper hole 19 agrees with the charging passage 24 and the lower hole 28 faces the storage chamber 20a, and the discharging hole 25 is closed by the wall of the cylinder 23b. When discharging particles 15, the cylinder 23*b* is placed in such a position that that the lower hole 28 agrees with the discharging passage 25 and the upper hole 28 faces the storage chamber 20*a*, and the charging hole 24 is closed by the wall of the cylinder 23*b*. When the particle charge chamber is applied with pressure, the charging passage 24 and the discharging passage 25 are closed by the wall of the cylinder 23*b*.

In the foregoing embodiment, moreover, pressurized air is supplied into the particle charge chamber 16 to make the contact member 11 come into tight contact with the gypsum bandage 64. However, medium other than air may be used such as water. In the same way, the expander member 17 can be inflated by a medium other than air, such as water.

Two particle supply units are provided in the foregoing embodiment. However, it may be possible to provide a single particle supply unit, or three or more particle supply units. The holder unit and the particle supply unit may be connected with two or more charging and discharging passages.

In the foregoing embodiment, one conveying device is provided in one particle supply unit. However, it may be appreciated to provide two or more conveying devices in one particle supply unit to increase the particle charging rate.

In the foregoing embodiment, the two particle supply units 20 are integrally attached to the holder unit 10, and are movable with the holder unit 10. However, it may be appreciated to place particle supply units on the floor and allow the holder unit 10 to move freely from the particle supply units. In this case, the charging and discharging passages 24 and 25 are made of flexible material instead of the metal material.

Furthermore, it may be appreciated to constitute an amputated part holding apparatus only by the holder unit 10 without providing any particle supply unit. In this case, particles are charged and discharged by hands.

In the foregoing embodiment, the supply of pressurized air into the particle charge chamber 16 is separately performed before the charging of particles. However, these operations may be performed at the same time.

Gypsum bandage is used as mould material in the foregoing embodiment. However, other material such as synthetic resin may be used.

It is not needless to say that an amputated part holding apparatus is not limited to making of a mould of an amputated leg, but applicable for making of a mould of other parts.

As described above, an inventive amputated part holding apparatus comprises a casing, a contact member provided in the casing to define a particle charge chamber between the contact member and the casing. The contact member is operable to come into contact with an amputated part owing to increased particles in the particle charge chamber. The casing is formed with a charging hole for charging particles into the particle charge chamber.

With this construction, the particle charge chamber is charged with particles. Accordingly, the amputated part is reliably supported by the pressing force produced by the charged particles, and can be consequently kept from moving down due to the weight even when the amputee takes the standing posture. Thus, it could be easily accomplished to make a mould reflecting the actual state of an amputated part that receives a body weight of the amputee in the standing posture. Also, the apparatus can provide a training machine by which an amputee virtually feels wearing of an artificial limb.

It may be preferable to further provide an expander member in the particle charge chamber to apply additional pressing forces to particles charged in the particle charge chamber. The expander member may preferably have an enclosed space for receiving a pressurized fluid. The expander member may be preferably formed by a flexible tube. The provision of the expander member is useful to set the particles in the chamber in the immovable state.

The casing may be further formed with a discharging hole, and further provided with a particle supply unit which includes a particle storage chamber for storing particles, a charging passage for connecting the charging hole of the casing with the particle storage chamber, a discharging passage for connecting the discharging hole of the casing with the particle storage chamber. The charging and discharging of particles can be reliably performed.

The charging hole may be formed in an upper portion of the casing while the discharging hole may be formed in a lower portion of the casing. Particles are charged from the upper portion of the casing, which ensures charging of more particles.

The particle supply unit may be further provided with a conveying device in the particle storage chamber for conveying particles from the particle storage chamber to the charging passage, and particles from the discharging passage to the particle storage chamber. The provision of the conveying device ensures automatic charging and discharging of particles.

The particle may be preferably made of synthetic resin. The use of synthetic resin particles reduces the production cost of particles, and facilitates handling of particles.

The amputated part holding apparatus may be further provided with a support unit for supporting the casing in such a way as to rotate in a predetermined axis. With this construction, the casing can be pivotally supported. Thus, the amputated part can be easily inserted in the space defined by the contact member, and maintained in the standing posture more reliably.

An inventive method for making a mould of an amputated part comprising the steps of attaching a mould material onto an amputated part, inserting the amputated part attached with a mould material into a space defined by a contact member which defines a particle charge chamber owing to a mechanical connection with a casing, charging particles into the particle charge chamber to cause the contact member to come into pressing contact with the mould material attached on the amputated part, keeping the amputated part in the space defined by the contact member until the mould material reaches a predetermined hardness, and discharging the particles from the particle charge chamber to allow the amputated part attached with the hardened mould material to withdraw from the space defined by the contact member.

Further, it may be preferable to provide the step of supplying a pressurized fluid into the particle charge chamber charged with particles to keep the particles in an immovable state.

In this method, an amputated part attached with mould material is supported by the particles charged in the particle charge chamber. When the body weight of the amputee is applied to the contact member, the amputated part is reliably kept from moving down. Accordingly, a mould reflecting actual conditions of the amputated part in the standing posture can be accurately made without the excellent skill of an artisan.

This application is based on patent application No. 2002-304836 filed in Japan, the contents of which are hereby incorporated by references.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. An amputated part holding apparatus comprising:
   a casing;
   a contact member provided in the casing to define a particle charge chamber between the contact member and the casing, the contact member being operable to come into contact with an amputated part owing to increased particles in the particle charge chamber; and
   a plurality of expander members provided in the particle charge chamber for applying additional pressing forces to particles charged in the particle charge chamber, each of the expander members being connected with a tube ring;
   wherein the casing is formed with a charging hole for charging particles into the particle charge chamber.

2. The amputated part holding apparatus according to claim 1, wherein each of the expander member has an enclosed space for receiving a pressurized fluid.

3. An amputated part holding apparatus comprising:
   a casing;
   a contact member provided in the casing to define a particle charge chamber between the contact member and the casing, the contact member being operable to come into contact with an amputated part owing to increased particles in the particle charge chamber; and
   wherein the casing is formed with a charging hole for charging particles into the particle charge chamber and with a discharging hole, and
   a particle supply unit including:
      a particle storage chamber for storing particles;
      a charging passage for connecting the charging hole of the casing with the particle storage chamber;
      a discharging passage for connecting the discharging hole of the casing with the particle storage chamber.

4. The amputated part holding apparatus according to claim 3, wherein the particle supply unit further includes a conveying device provided in the particle storage chamber for conveying particles from the particle storage chamber to the charging passage, and particles from the discharging passage to the particle storage chamber.

5. The amputated part holding apparatus according to claim 1, wherein the particles are made of synthetic resin.

6. The amputated part holding apparatus according to claim 3, further comprising a support unit for supporting the casing in such a way as to rotate in a predetermined axis.

* * * * *